United States Patent
Agrawal et al.

(10) Patent No.: US 10,957,420 B2
(45) Date of Patent: Mar. 23, 2021

(54) SECURE TRANSMISSION OF GENOMIC DATA

(71) Applicant: KONINKLIJKE PHILIPS N.V., Eindhoven (NL)

(72) Inventors: Vartika Agrawal, Cambridge, MA (US); Nevenka Dimitrova, Pelham Manor, NY (US); Raymond J. Krasinski, Suffern, NY (US)

(73) Assignee: Koninklijke Philips N.V., Eindhovern (NL)

( * ) Notice: Subject to any disclaimer, the term of this patent is extended or adjusted under 35 U.S.C. 154(b) by 378 days.

(21) Appl. No.: 15/529,109

(22) PCT Filed: Nov. 18, 2015

(86) PCT No.: PCT/IB2015/058912
§ 371 (c)(1),
(2) Date: May 24, 2017

(87) PCT Pub. No.: WO2016/083949
PCT Pub. Date: Jun. 2, 2016

(65) Prior Publication Data
US 2017/0262579 A1 Sep. 14, 2017

Related U.S. Application Data

(60) Provisional application No. 62/084,146, filed on Nov. 25, 2014.

(51) Int. Cl.
| | | |
|---|---|---|
| *G01N 33/48* | (2006.01) | |
| *G01N 33/50* | (2006.01) | |
| *G16B 20/00* | (2019.01) | |
| *G16B 30/00* | (2019.01) | |
| *G16B 50/00* | (2019.01) | |
| *G06F 21/62* | (2013.01) | |
| *H03M 7/30* | (2006.01) | |
| *G06F 21/60* | (2013.01) | |
| *H04L 29/06* | (2006.01) | |
| *G16H 10/60* | (2018.01) | |

(52) U.S. Cl.
CPC .......... *G16B 20/00* (2019.02); *G06F 21/606* (2013.01); *G06F 21/6245* (2013.01); *G16B 30/00* (2019.02); *G16B 50/00* (2019.02); *H03M 7/30* (2013.01); *H03M 7/3059* (2013.01); *H04L 63/0428* (2013.01); *G16H 10/60* (2018.01)

(58) Field of Classification Search
CPC ........ G16B 20/00; G16B 30/00; G16B 50/00; H03M 7/30; H03M 7/3059; G06F 21/606; G06F 21/6245; H04L 63/0428; G16H 10/60
See application file for complete search history.

(56) References Cited

U.S. PATENT DOCUMENTS

| | | | |
|---|---|---|---|
| 2005/0058215 A1 | 3/2005 | Biswas et al. | |
| 2011/0288785 A1 | 11/2011 | Tembe | |
| 2012/0102054 A1 | 4/2012 | Popescu et al. | |
| 2012/0230326 A1 | 9/2012 | Ganeshalingam et al. | |
| 2013/0245958 A1* | 9/2013 | Forster ................ | G16B 30/00 702/19 |
| 2013/0246460 A1 | 9/2013 | Maltbie et al. | |
| 2014/0040264 A1 | 2/2014 | Varaday et al. | |
| 2014/0200166 A1* | 7/2014 | Van Rooyen .......... | G16B 30/00 506/38 |

FOREIGN PATENT DOCUMENTS

| | | |
|---|---|---|
| JP | 2007506372 A | 3/2007 |
| JP | 2014523589 A | 9/2014 |
| WO | 2013009890 A2 | 1/2013 |
| WO | 2013049420 A1 | 4/2013 |
| WO | 2014144478 A2 | 9/2014 |
| WO | 2013067001 A1 | 5/2015 |

OTHER PUBLICATIONS

Singh et al: "METASEQ: Privacy Preserving Meta-Analysis of Sequencing-Based Association Studies" In: "Biocomputing 2013", Nov. 2012 (Nov. 1, 2012), World Scientific, XP055249207,ISBN: 978-981-4447-97-3 pp. 356-367.
S. Deorowicz et al: "Genome compression: a novel approach for large collections", Bioinformatics., vol. 29, No. 20, Oct. 15, 2013 (Oct. 15, 2013), pp. 2572-2578.

* cited by examiner

Primary Examiner — Russell S Negin

(57) ABSTRACT

The amount of genomic data as well the sensitivity of the information carried necessitates the need to develop smart and efficient ways to transmit genomic data in a secure way. While encryption schemes exist, there is also the need to first reduce the amount of massive information and then apply an encoding and encryption method that will be effective both in the economic sense as well as for security of genomic data. In this invention, we discuss novel techniques to encode processed variant information and send it across to a remote site ensuring covert transmission. The protocols not only encode and encrypts the information; it condenses the information that needs to be transferred.

4 Claims, 3 Drawing Sheets

SECURE TRANSMISSION OF GENOMIC DATA

TECHNICAL FIELD

Embodiments of the invention generally relate to secure data transfer, and more particularly to systems and methods for the secure transfer of large amounts of data that are subject to privacy restrictions and other security concerns over otherwise unsecure networks.

BACKGROUND

Sequencing techniques, such as genomic sequencing and SNP genotyping, can generate a large amount of genomic data. For example, a variant call file used to store data from sequencing variants of a chromosome may be hundreds of gigabytes.

Researchers and healthcare providers frequently need to transfer genomic data from one site to another geographically distant site. Because dedicated or private networks that span long distances can be prohibitively expensive or otherwise include unsecure spans, the data is often transferred over non-secure networks. Genomic data may be associated with particular patients and so there are privacy concerns; indeed, the transfer may be subject to laws and regulations related to the storage and transfer of such data. Further, as the data is processed to identify patient-specific anomalies, the more sensitive the information and therefore the greater need for a secure transfer mechanism.

The amount of data as well as the sensitivity of the information necessitates the need to develop efficient techniques to transmit genomic data securely. Existing techniques do not necessarily account for the characteristics of the genomic data, including variant data, nor take into account the quality of the specific data being transferred.

Accordingly, there is a need for an efficient and secure system for transferring genomic data over unsecure networks.

SUMMARY

In general, various aspects of the systems, methods, and apparatus described herein are directed toward improved systems and methods for transferring genomic data among geographically distant sites over unsecure networks through novel techniques of processing, reducing, encoding, and encrypting the data before transfer. Particular detail is presented for applying the system to transferring variant information consisting of single nucleotide polymorphisms (SNPs), but those of ordinary skill in the art will recognize the embodiments described herein have broader applications.

According to one aspect of the present invention a system for transforming data sequenced from a genome and processed into a variant call file (VCF) includes a first and a second processing module each comprising a computer processor and a computer readable tangible medium. The first processing module is operable to reduce the VCF into an annotated VCF that comprises primarily non-redundant variant data from the VCF based on reference data, encode the annotated VCF; and store the encoded VCF. The second processing module is operable to receive the encoded VCF, and inflate the encoded VCF.

In one embodiment, the reference data includes reference and alternate allele data from a database of short genomic variations (SNP). In one embodiment, encoding the annotated VCF comprises converting chromosome number and chromosome position data of the annotated VCF using a mathematical coordinate system.

According to another aspect of the present invention a method, performed by a computer processor, of transforming data sequenced from a genome of a patient and processed into a variant call file (VCF) is provided, and includes the steps of reducing the VCF into an annotated VCF that comprises primarily non-redundant variant data from the VCF, encoding the annotated VCF, and storing the encoded VCF on a computer readable tangible medium.

In one embodiment, reducing the VCF includes removing variant calls whose associated quality data does not meet a predetermined threshold. In one embodiment, reducing the VCF includes removing known variants using a reference database of short genomic variations (SNP) data. The known variants may include one or more of reference and alternate allele information.

In one embodiment, encoding the annotated VCF includes converting chromosome number and chromosome position data of the annotated VCF using a mathematical coordinate system. Converting the chromosome number and chromosome position data of the annotated VCF using a mathematical coordinate system may include converting the chromosome number and chromosome position data of the annotated VCF to a cyclic coordinate system based on a modulus value. The method may further include encrypting the modulus value and initiating transfer of the encrypted modulus value and the encoded VCF file to a second terminal over a network connection.

In one embodiment encoding the annotated VCF includes converting chromosome number and chromosome position data of the annotated VCF using one of Cartesian coordinates, polar coordinates, or linear coordinates. In one embodiment, the method also includes applying a frequency domain transform to the annotated VCF prior to encoding the annotated VCF. In one embodiment, the method also includes transferring the encoded VCF to a second terminal over a network connection.

According to another aspect of the present invention a method, performed by a computer processor, of transforming data sequenced from a genome of a patient and processed into a variant call file (VCF) is provided, and includes the steps of receiving a VCF encoded using a mathematical coordinate system; and inflating the encoded VCF with reference and alternate allele data using a reference database of short genomic variations (SNP) data.

In one embodiment, the method further includes decoding the encoded VCF using a modulus value.

The foregoing and other features and advantages of the present invention will be made more apparent from the descriptions, drawings, and claims that follow. One of ordinary skill in the art, based on this disclosure, would understand that other aspects and advantages of the present invention exist.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

Described herein are various embodiments of methods and systems consistent with the present invention. These embodiments are exemplary and should not be interpreted to limit the scope that one of ordinary skill in the art would give to the invention.

Genomic data is output from sequencing machines as known to those having ordinary skill in the art. The amount of raw data output from a sequencing machine can be hundreds of gigabytes in size. The raw data is typically compared against and aligned to a reference genome to create an alignment file, e.g., a variant call file (VCF), that is orders of magnitude smaller than the raw data, but still too large for ready transfer to a remote site.

Figure 1:
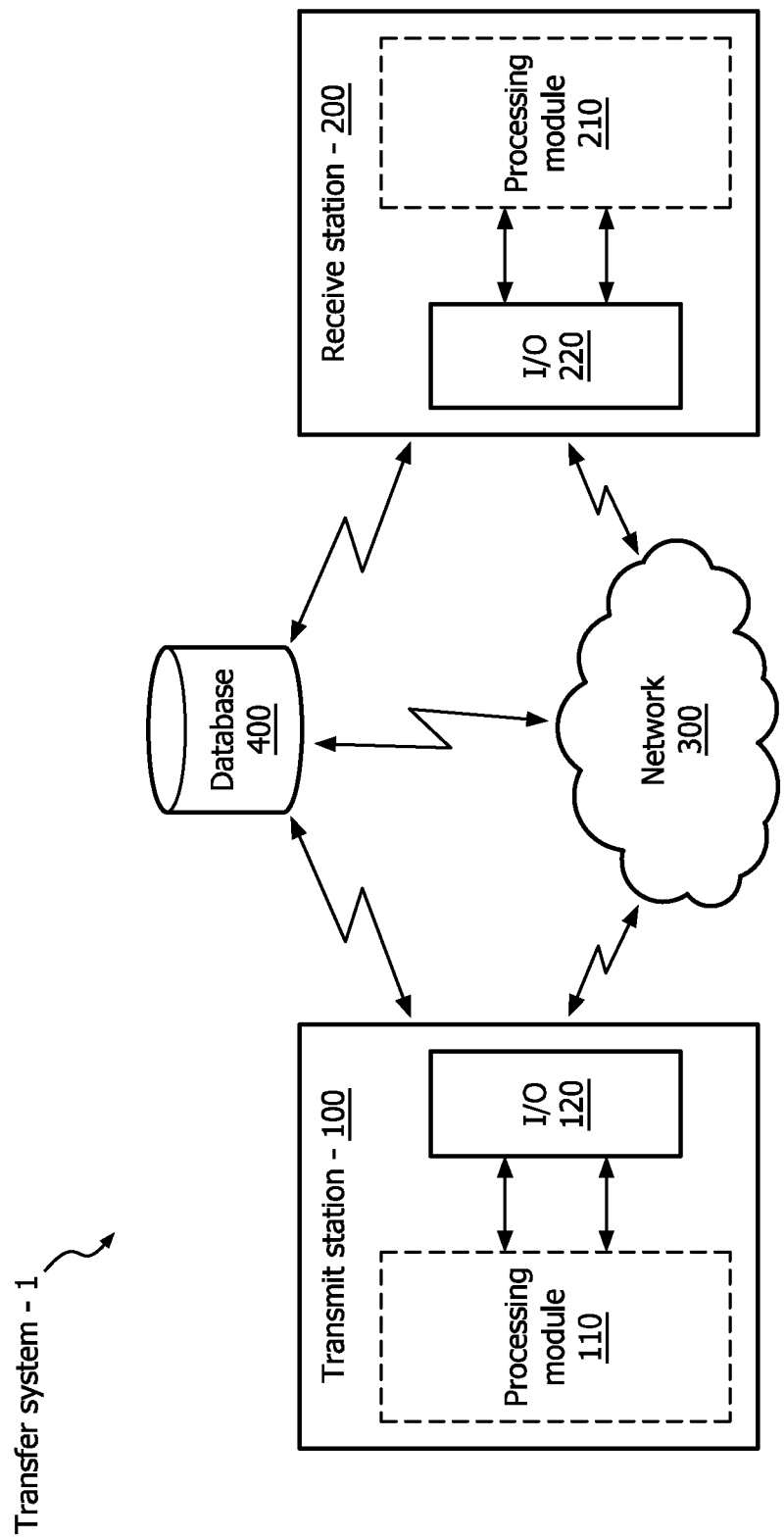
FIG. 1 is a diagram of a secure transfer system according to an exemplary embodiment of the present invention.

An exemplary embodiment of a system for the secure transfer of genomic data over otherwise unsecure networks is illustrated in FIG. 1. The Transfer System 1 includes a Transmit Station 100, a Receive Station 200, a Network 300, and Database 400.

The Transmit Station 100 includes a Processing Module 110 and an I/O Unit 120. The Processing Module 110 processes the VCF file to produce a reduced file as discussed below for secure transfer to the Receive Station 200 that is typically remote from the Transmit Station 100. The I/O Unit 120 handles the transmission of the reduced file, which may also be encrypted and/or encoded.

The Receive Station 200 includes a Processing Module 210 and an I/O Unit 220. The I/O Unit 220 handles the receipt of the reduced file, which may also be encrypted and encoded. The Processing Module 210 processes and restores the reduced file to the original VCF file or something similar.

In Transfer System 1, the reduced, encoded and encrypted file is transmitted at least in part over the Network 300. The Network 300 may be comprised of, or may interface to, any one or more of the Internet, an intranet, a personal area network (PAN), a local area network (LAN), a wide area network (WAN), etc.

Database 400 includes genomic data information that may be relevant to the alignment file, i.e., the data that had been previously aligned to a reference genome. If any of the data from the alignment file is present in the Database 400 then the alignment file may be annotated with reference information from the Database 400, the annotations themselves substituting for data that is otherwise stored in the Database 400 and accessible by the Receive Station 200.

For example, in one exemplary embodiment the file that has been previously aligned to reference genome data is a variant call file (VCF) of variant data and the Database 400 is a resource of known variants, e.g., a database of SNP data. Databases of SNP data are known to those having ordinary skill in the art, and are maintained, for example, by the National Center for Biotechnology Information at the National Institutes for Health.

A typical entry in a VCF includes the following information that is relevant to the reconstruction of the genome: the chromosome on which the single nucleotide variant (or small insertion or deletion) is located, position on the chromosome, reference base (A, C, G, T, or N), alternate base (A, C, G, or T), quality of the variant call, and the nature of the variant call (homozygous/heterozygous). An entry in a VCF may include other information that is not relevant to the reconstruction process discussed here.

For known variants in the VCF, the genomic coordinates for the position on a chromosome are enough to determine the reference and the alternate allele data for the variant from the information stored in the database of SNP data and thus can be used to reduce a VCF. Chromosome coordinates comprise the chromosome number and position of the variant on the chromosome.

Database 400 may be a searchable database and may comprise, include or interface to a relational database. Other databases, such as a query format database, a Standard Query Language (SQL) format database, or a similar data storage device, query format, platform or resource may be used. Database 400 may comprise a single database or a collection of databases, dedicated or otherwise. In one embodiment, Database 400 may store or cooperate with other databases to store the various data and information described herein. In some embodiments, Databases 400 may comprise a file management system, program or application for storing and maintaining data and information used or generated by the various features and functions of the systems and methods described herein.

Figure 2:
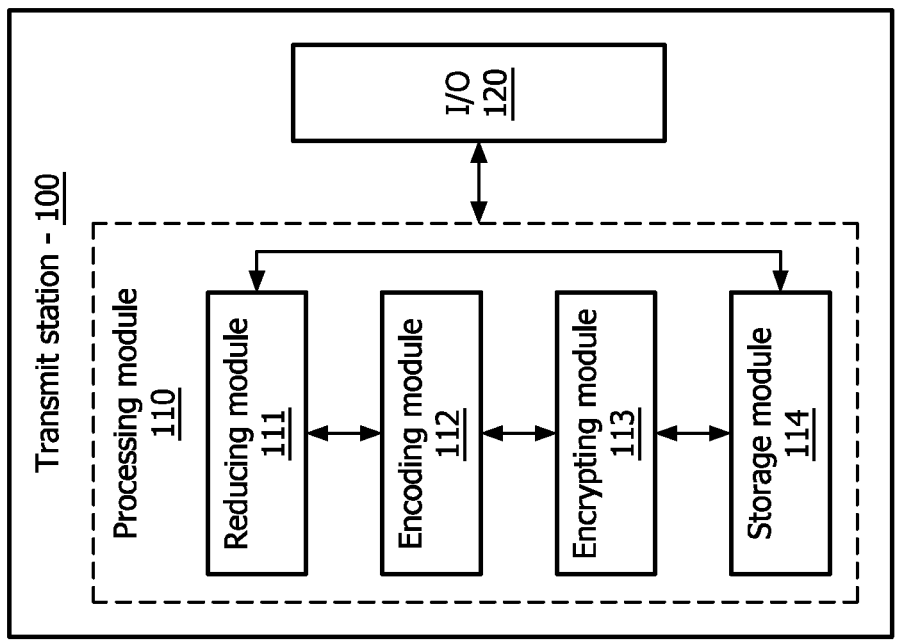
FIG. 2 is an illustration of a transmit station according to an exemplary embodiment of the present invention.

An exemplary embodiment of the Transmit Station 100 is illustrated in FIG. 2. The Processing Module 110 includes a Reducing Module 111, an Encoding Module 112, an Encrypting Module 113, and a Storage Module 114. The Reducing Module 111 reduces a previously aligned data file or VCF, for example, using annotations based on known genomic data stored in a database or other techniques that are more fully described herein.

The Encoding Module 112 encodes the reduced file. In the example of a VCF that has been reduced, the Encoding Module 112 may replace the variant data with the genomic coordinates, i.e., chromosome number and position, encoded using a coordinate system (e.g., Cartesian, Polar, etc.) as discussed in greater detail below. The Encrypting Module 113 encrypts the VCF using encryption techniques known to the art, such as symmetric or asymmetrical encryption. The Storage Module 114 may store the result of the reducing, encoding, and encryption performed by the Reducing Module 111, the Encoding Module 112, and the Encrypting Module 113, as well as intermediate steps thereof.

Figure 3:
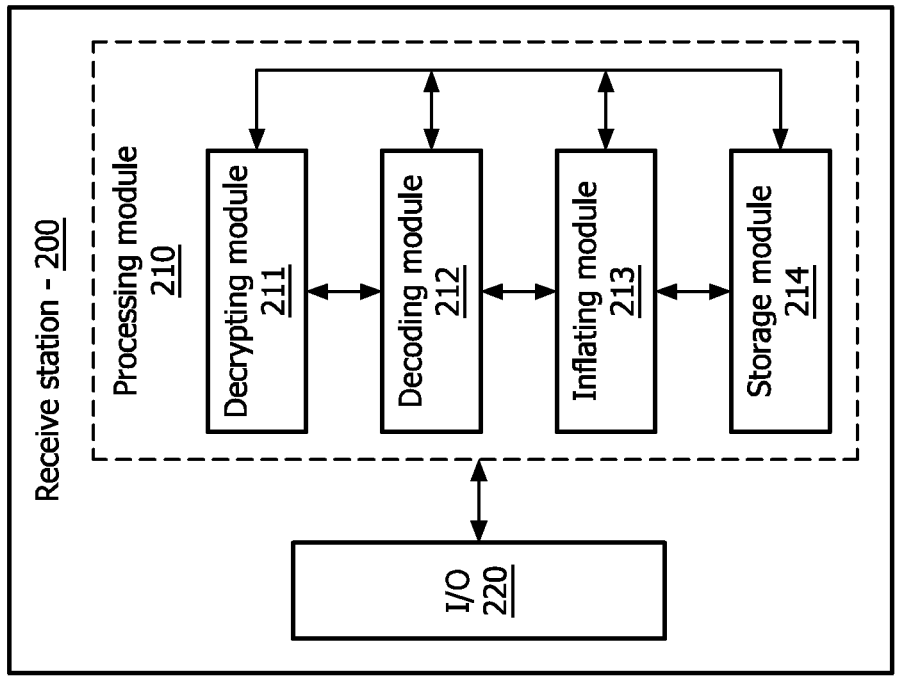
FIG. 3 is an illustration of a receive station according to an exemplary embodiment of the present invention.

An exemplary embodiment of the Receive Station 200 is illustrated in FIG. 3. The Processing Module 210 of the Receive Station 200 includes a Decrypting Module 211, Decoding Module 212, Inflating Module 213, and a Storage Module 214. The Decrypting Module 211 decrypts an encrypted genomic data file received via I/O unit 220. The Decoding Module 212 decodes the encoded file received from the Transmit Station 100 using the coordinate scheme employed during the encoding process. The Inflating Module 213 inflates the decoded reduced file. In the example of a VCF that was reduced with reference to known variant data stored on a dbSNP, the same database or one containing the same information may be used to replace the annotations in the reduced VCF with the corresponding genomic data. For example, the alternate and reference allele data could be looked up in the dbSNP and "re-added" to the VCF entries.

An exemplary operation of the Transfer System 1 to transfer a VCF will now be described with reference to FIGS. 4 and 5. The Transmit Station 100 receives the sequenced genomic data (Step S100). The sequenced data may be unprocessed or it might have been previously aligned to a reference genome. If it has not been previously aligned to a reference genome, the sequenced genomic data is processed and aligned with a reference genome (Step S101). Next, the Reducing Module 111 reduces the VCF (Step S102). To reduce the VCF, reference is made to a database of known variants (dbSNP), typically indexed by chromosome. For each data entry in the VCF, if the variant is already known then the information in the entry may be reduced to the chromosome and the position of the variant on the chromosome. The more information stored in the dbSNP, the more the VCF may potentially be reduced.

According to one exemplary embodiment, removing variant data that does not meet a predetermined quality threshold may further reduce the variant data in the VCF. The reconstruction of the genome is more reliable when the variant calls are robust (of higher quality). In this exemplary embodiment, variant calls meeting the predetermined quality threshold are kept and the lower quality variant calls are removed or skipped in the creation of the file for transfer. Those of ordinary skill in the art would understand that the threshold for variant quality might vary depending on the type of variant caller being used. For example, with Illumina next generation sequencing data, at least 20 reads covering the SNP would be needed.

Next, the reduced VCF may be encoded to further shrink the size of the file (Step S103). Encoding the genomic coordinates, namely chromosome number and position, may, according to one exemplary embodiment, be accomplished using a coordinate system. Any suitable coordinate system may be used, though according to the exemplary embodiments described herein Cartesian, Polar, Linear, and Cyclic coordinate systems are used.

Cartesian Coordinate Encoding

The translation of genomic coordinates into Cartesian coordinates may be performed by placing the set of chromosomes at issue (e.g., a 24 chromosome set) on an x-axis in a way that the center of the chromosome lies on the x-axis, namely if the y coordinate of the center of each chromosome is zero.

While the range of the x coordinates is, e.g., [1 . . . 24], the range of the y coordinates will be [−α/2 . . . α/2] where a is the number of nucleotide bases present on the chromosome. For each chromosome, the axis coordinate y=0 will be shifted to a new position α' where:

$$\alpha' = \begin{cases} \text{Quotient } (\alpha/2) + 1, \text{ if } \alpha = 2k+1, k >= 0 \\ \text{Quotient } (\alpha/2), \text{ if } \alpha \text{ is } 2k, k >= 0 \end{cases} \quad \text{EQUATION 1}$$

Polar Coordinates

The polar coordinates (r, θ) which represent the length (radius) and angle for genomic locations may be obtained by translation from the Cartesian coordinates (x, y) above such that:

$$x = r \cos \theta$$

$$y = r \sin \theta$$

$$r = \sqrt{(x^2 + y^2)}$$

$$\theta = \cos^{-1}(x/r) = \sin^{-1}(y/r) \quad \text{EQUATION 2}$$

Linear Coordinates

Linear coordinates may be obtained by the translation of the genome from its organization into chromosomes into a single string of ~3 billion base pairs (the number of base pairs in the human genome). This translation may be performed by concatenating the nucleotide bases from each of the chromosomes into one string in the conventional chromosomal order (chr1 . . . chr22 followed by chrX and chrY respectively). Therefore the range of the linear coordinates will be a ∈[1 . . . 3,209,286,105].

Cyclic Coordinates

To obtain cyclic coordinates the chromosomal positions are mapped to a cyclic (circular) coordinate system where points on a circle represent the nucleotide positions and the angular distance of these points represents the position coordinate. If the number of positions exceeds the number of representations possible in a span of 1 rotation (2π), modular arithmetic can be used to scale down the values.

In one exemplary embodiment a modular arithmetic value may be used to reduce the complexity of VCF encoded using a cyclic coordinate system. Using a modulus (n) to wrap the positions around, the linear value of the position a may be converted into a position on a circle as follows:

$$a = n \times q + r$$

$$q \in Z \text{ \& } |r|<|n| \quad \text{EQUATION 3}$$

The translated coordinate a'=f(n, q, r) where n is modulus value, q is the quotient of the division and r is the remainder. For each position in the VCF file, the encoded file will have the following information: (i) quotient of the modulus operation; (ii) remainder of the modulus operation expressed as an angle; and (iii) alternate allele at the position.

The modulus value, "n," may serve as a key to decode the information in the VCF. The modulus value may be a constant or may be calculated by a random number generator. The modules value may be sent with the VCF or, alternatively, sent via a different channel. In one exemplary embodiment the other channel is a secure channel. A secure channel may also be used, for example, to transmit patient identifying information.

The modulus value may be encrypted using encryption techniques known to those having ordinary skill in the art. In this exemplary embodiment where a modulus value is utilized, in order to decode the variant information of the patient, the remote site will be required to decrypt the modulus value and then decode the variant coordinates thereby undergoing two levels of decryption.

After the reducing and encoding steps, the condensed and encoded VCF may be encrypted by the Encrypting Module 113 (Step S104). Any suitable encryption technique may be utilized, including symmetric and asymmetric encryption techniques.

In one exemplary embodiment the encryption step may be preceded by a step of DNA spectral analysis in which the A, C, G, and T bases of the alternative alleles is transformed into the spectral domain using, for example, a Fourier or other frequency transform. Upon receipt the spectral DNA would be transformed back to A, C, G, and T bases of the alternative alleles.

Figures 4, 5:
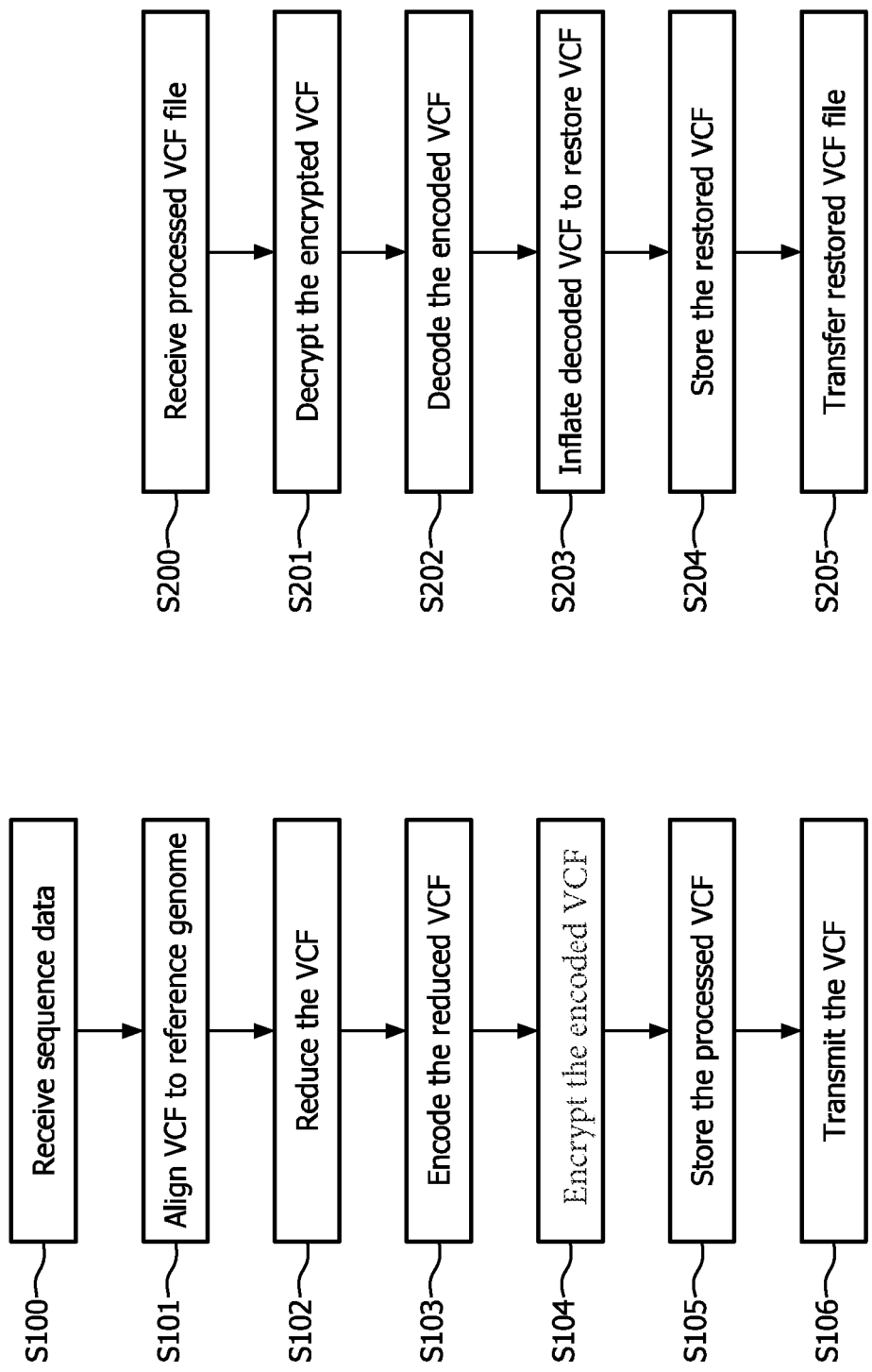
FIG. 4 is a flow chart illustrating an exemplary operation of the transmit station illustrated in FIG. 2.
FIG. 5 is a flow chart illustrating an exemplary operation of the receive station illustrated in FIG. 3.

During the operation described in FIG. 4, the results of the various steps may be stored, including after the encryption step (Step S105).

The processed file may then be transferred to the Receive Station 200 over the Network 300, which may be insecure or include insecure spans. Restoration of the original file at the Receive Station 200 according to an exemplary embodiment of the present invention will now be described with reference to FIG. 5. The process of restoring is essentially the process of applying the reducing, encoding and encrypting steps that were applied to the transmitted file in reverse.

If the file has been decrypted then the encrypted file is decrypted by the Decrypting Module 211 (Step S201). In the exemplary embodiment including the step of frequency transform into the spectral domain, the spectral DNA information would be transformed back to the A, C, G, T bases of the alternative alleles. In one exemplary embodiment the encryption scheme used by the Encryption Module 113 is known in advance to the Decryption Module 211. In another exemplary embodiment the encoding scheme is transferred to the Decryption Module 211 with the transferred file or after the transfer of the file, using the same or a separate channel.

In the embodiment where a modulus value was used in the encryption process then that value is decrypted and then used by the Decrypting Module 211 to perform the decryption of the encrypted VCF.

Next, the Decoding Module 212 decodes the decrypted file (Step S202). In one exemplary embodiment the encoding scheme used by the Encoding Module 112 is known to the Decoding Module 212 in advance. In another exemplary embodiment the encoding scheme is transferred to the Decoding Module 212 with the transferred file or after the transfer of the file, using the same or a separate channel.

Next the Inflating Module 213 inflates the decoded file with reference to the database of known variants (Step S203). During the operation described in FIG. 5, the results of the various steps may be stored, including storing the restored VCF after the final inflating step (Step S204). Upon restoration the VCF may be transferred as needed for further processing (Step S205).

The Transmit Station 100 and Receive Station 200 may be incorporated into computer stations where operations are initiated by a human operator, automatic operation, or both. The Transmit Station 100 may also be incorporated into a network device (such as a server or router) that includes the capability to identify a VCF that is being transferred and perform the exemplary operations described herein. The network device may be a gateway that routes data between the network where the sequenced genomic data is reduced, encoded and encrypted according to exemplary embodiments described herein, through networks over which such data is transferred, to a network including the Receive Station 200. The Receive Station 200 may also be included in a network device (such a network gateway) that includes the capability to identify a reduced, encoded and encrypted VCF according to exemplary embodiments described herein and restore the genomic data.

The transfer system as shown in FIGS. 1, 2 and 3 may be or include a computer system. The transfer system may be described in the general context of computer-executable instructions, such as program modules, being executed by a computer. Generally, program modules include routines, programs, objects, components, data structures, etc., that perform particular tasks or implement particular abstract data types.

Those skilled in the art will appreciate that the invention may be practiced with various computer system configurations, including hand-held wireless devices such as mobile phones or tablets, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote computer storage media including memory storage devices.

The transfer system may include a plurality of software processing modules stored in a memory as described above and executed on a processor in the manner described herein. The program modules may be in the form of any suitable programming language, which is converted to machine language or object code to allow the processor or processors to execute the instructions.

The computer system may include a general-purpose computing device in the form of a computer including a processing unit, a system memory, and a system bus that couples various system components including the system memory to the processing unit.

The processing unit that executes commands and instructions may be a general purpose computer, but may utilize any of a wide variety of other technologies including a special purpose computer, a microcomputer, mini-computer, mainframe computer, programmed micro-processor, micro-controller, peripheral integrated circuit element, a CSIC (Customer Specific Integrated Circuit), ASIC (Application Specific Integrated Circuit), a logic circuit, a digital signal processor, a programmable logic device such as an FPGA (Field Programmable Gate Array), PLD (Programmable Logic Device), PLA (Programmable Logic Array), RFID integrated circuits, smart chip, or any other device or arrangement of devices that is capable of implementing the steps of the processes of the invention.

It should be appreciated that the processors and/or memories of the computer system need not be physically in the same location. Each of the processors and each of the memories used by the computer system may be in geographically distinct locations and be connected so as to communicate with each other in any suitable manner. Additionally, it is appreciated that each of the processor and/or memory may be composed of different physical pieces of equipment.

The computing environment may also include other removable/non-removable, volatile/nonvolatile computer storage media.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A computer-implemented method of transforming data sequenced from a genome of a patient and processed into a variant call file (VCF), the method comprising:
  providing a computer processor configured to:
    reduce the VCF into an annotated VCF that comprises primarily non-redundant variant data from the VCF, wherein annotations of the annotated VCF include genome coordinate data stored in a genomic database;
    encoding the annotated VCF by converting chromosome number and chromosome position data of the annotated VCF to a cyclic coordinate system based on a modulus value;

and storing the encoded VCF on a computer readable tangible medium.

2. The method of claim 1, further comprising encrypting the modulus value and initiating transfer of the encrypted modulus value and the encoded VCF file to a second terminal over a network connection.

3. The method of claim 1 wherein encoding the annotated VCF further comprises converting chromosome number and chromosome position data of the annotated VCF using one of Cartesian coordinates, polar coordinates, or linear coordinates.

4. A computer-implemented method of transforming data sequenced from a genome of a patient and processed into a variant call file (VCF), the method comprising:
  providing a computer processor configured to:
    receive an encoded VCF that is annotated with genome coordinate data stored in a genomic database;
    inflate the encoded VCF with reference and alternate allele data using a reference database of short genomic variations (SNP) data; and
    decode the encoded VCF using a modulus value.

* * * * *